United States Patent [19]

Young

[11] Patent Number: 5,055,127
[45] Date of Patent: * Oct. 8, 1991

[54] VEGETATION CONTROL WITH MONOUREA SULFURIC ACID

[75] Inventor: Donald C. Young, Fullerton, Calif.
[73] Assignee: Union Oil Company of California, Los Angeles, Calif.
[*] Notice: The portion of the term of this patent subsequent to Jul. 23, 2008 has been disclaimed.
[21] Appl. No.: 235,005
[22] Filed: Aug. 22, 1988

Related U.S. Application Data

[62] Division of Ser. No. 444,667, Nov. 26, 1982, abandoned.
[51] Int. Cl.$^5$ .................... A01N 47/28; A01N 59/02
[52] U.S. Cl. ....................................... 71/83; 71/119
[58] Field of Search ........................... 71/65, 83, 119

[56] References Cited

U.S. PATENT DOCUMENTS

| | | | |
|---|---|---|---|
| 1,340,708 | 5/1920 | Fjellanger | 71/28 |
| 4,116,664 | 9/1978 | Jones | 71/29 |
| 4,214,888 | 7/1980 | Young | 71/28 |
| 4,310,343 | 1/1982 | Verdegaal et al. | 71/28 |
| 4,315,763 | 2/1982 | Stoller et al. | 71/29 |
| 4,336,052 | 6/1982 | Chen et al. | 71/DIG. 1 |
| 4,397,675 | 8/1983 | Young | 71/28 |
| 4,402,852 | 9/1983 | Young | 252/182 |
| 4,404,116 | 9/1983 | Young | 252/182 |
| 4,445,925 | 5/1984 | Young | 71/28 |
| 4,447,253 | 5/1984 | Young | 71/28 |
| 4,512,813 | 4/1985 | Young | 134/27 |
| 4,522,644 | 6/1985 | Young | 71/78 |
| 4,589,925 | 5/1986 | Young | 134/3 |
| 4,626,417 | 12/1986 | Young | 423/235 |
| 4,664,717 | 5/1987 | Young | 127/37 |
| 4,673,522 | 6/1987 | Young | 252/87 |
| 4,686,017 | 8/1987 | Young | 204/45.1 |
| 4,722,986 | 2/1988 | Young | 527/203 |
| 4,743,669 | 5/1988 | Young | 527/200 |
| 4,755,265 | 7/1989 | Young | 204/45.1 |
| 4,801,511 | 1/1989 | Young | 429/204 |
| 4,818,269 | 4/1989 | Young | 71/83 |
| 4,831,056 | 5/1989 | Young | 514/588 |
| 4,834,788 | 5/1989 | Young | 71/78 |
| 4,839,088 | 6/1989 | Young | 252/183 |
| 4,877,869 | 10/1989 | Young | 536/35 |
| 4,885,425 | 12/1989 | Young | 585/458 |
| 4,910,356 | 3/1990 | Young | 585/262 |

FOREIGN PATENT DOCUMENTS 0164466 12/1933 Switzerland .................... 71/65

OTHER PUBLICATIONS

Code of Federal Regulations, Title 40, "Protection of Environment," Part 180, Subpart D, Section 180.1019, 7/1/80.
Chan et al., Chem. Abst., vol. 88, 1978, 13, 1876e.
Kamilova et al., Chem. Abst., vol. 94, 1981, 97847h.
Adalla, Chem. Abst., vol. 93, 1980, 90069(b).
Bach et al., Chem. Abst., vol. 95, 1981, 37118g.
Takala, Chem. Abst., vol. 90, 1979, 49658t.
Int. Dev. Oil. Palm. Proc. Malax. Int. Agric. Oil Palm. Conf., Incidental uses of . . . , 37MXAH, 1977.
The Condensed Chemical Dictionary, 7th. Ed., Van Nostrand Reinhold Co., New York, 1969, p. 908.
D. F. du Toit, Verslag Akad. Wetenschappen, 22, 573–4 (abstracted in Chemical Abstracts, 8, 2346, 1914).
L. H. Dalman, "Ternary Systems of Urea and Acid. I. Urea, Nitric Acid and Water. II. Urea, Sulfuric Acid and Water. III. Urea, Oxalic Acid and Water"; JACS, 56, 549–53 (1934).
Sulfur Institute Bulletin, No. 10 (1964), "Adding Plant Nutrient Sulfur to Fertilizer".
Farm Chemicals Handbook, Meister Publishing Co., Willoughby, Ohio (1981) p. C-316.

Primary Examiner—Richard L. Raymond
Assistant Examiner—Brian Bembenick
Attorney, Agent, or Firm—Gregory F. Wirzbicki; Michael H. Laird

[57] ABSTRACT

Methods for controlling vegetation are disclosed which involve contacting the foliage of the vegetation with an aqueous solution containing urea and sulfuric acid. The molar ratio of urea to sulfuric acid preferably is within the range of about ¼ to about 7/4 so that at least about 25 percent of the sulfuric acid is present in the solution as the monourea-sulfuric acid adduct. Methods for the selective control of undesired vegetation is seeded areas or in the presence of desired crop plants, nonselective methods of vegetation control involving the use of surfactant-containing solutions, and solid compositions suitable for producing the described aqueous solutions are also disclosed.

35 Claims, 1 Drawing Sheet

VEGETATION CONTROL WITH MONOUREA SULFURIC ACID

This application is a division of application Ser. No. 444,667, filed Nov. 26, 1982 (now abandoned).

BACKGROUND OF THE INVENTION

1. Field of the Invention

This invention relates to methods of controlling vegetation, and particularly to the use of contact herbicides for the general or selective control of vegetation.

2. Description of the Art

Both urea and sulfuric acid are widely used for a variety of purposes in numerous industries as fertilizers, soil adjuvants, chemical treating agents, chemical precursors and reactants. They are sometimes useful in combination, particularly in the agricultural industry, when the simultaneous addition of urea and sulfur to the soil is desired. Sulfuric acid is known to be phytotoxic, has been used as a postemergent, contact herbicide on a variety of plants, and is registered with the U.S. Environmental Protection Agency for the elimination of certain weed plants from plots of growing onions and garlic.

It has also been disclosed that urea will react with sulfuric acid to produce combinations of urea and sulfuric acid that are useful as fertilizers and soil treating agents.

Although sulfuric acid is an effective contact herbicide, it is relatively nonselective in that it damages essentially all foliage it contacts, and it is rapidly consumed by reaction with plant tissue. Thus, substantial quantities of sulfuric acid are required to obtain any effective degree of vegetation control. Furthermore, sulfuric acid is highly corrosive to many materials, including animal tissue, and thus is difficult to transport and distribute and requires the strict observance of safety practices to prevent injury to personnel involved in its application.

Although some investigators have disclosed that certain combinations of urea and sulfuric acid can be manufactured, they have not disclosed any method capable of producing significant, if any, quantities of the higher acid content compositions which contain a significant amount of the monourea-sulfuric acid adduct. Nor were their processes capable of producing urea-sulfuric acid reaction products free of decomposition products. The decomposition of urea and sulfuric acid upon their interaction can result in the formation of toxic materials such as sulfamic acid and ammonium sulfamate which are undesirable in certain applications Such decomposition can invariably result in the loss of sulfuric acid activity due to conversion of the acid to sulfamic acid, ammonium sulfamate, ammonium sulfate or other decomposition products. The presence of such decomposition products in the herbicidal composition of this invention does not contribute to herbicidal activity and, in some instances, is undesirable.

Many contact herbicides other than sulfuric acid are known and are widely used for the control of vegetation. However, many if not all of these have significant ecotoxic effects and are relatively expensive to manufacture. Furthermore, few, if any, of the alternative herbicides contribute significant, if any, quantities of nutrients or beneficial soil adjuvants to the plant environment. Most alternative contact herbicides are also toxic to humans. Thus, their use requires the observance of safety precautions sufficient to avoid harm to personnel involved in their application. Accordingly, a need exists for improved methods of vegetation control that minimize or eliminate these and other deficiencies of existing methods.

It is, therefore, a principal object of this invention to provide improved methods of vegetation control.

Another object of this invention is the provision of methods of vegetation control that are relatively nonhazardous to applicators and to the environment.

Another object is the provision of methods of vegetation control that result in the addition of significant amounts of plant nutrients and beneficial soil adjuvants to the plant environment.

Another object of this invention is the provision of methods for selectively eliminating undesired vegetation from the vicinity of desired vegetation.

Another object is the provision of methods for controlling undesired vegetation that do not result in the addition of toxic materials to the environment or to crops growing or subsequently planted in the treated area.

Another object is the provision of methods for controlling undesired vegetation that are more efficient than previously available methods and that thereby reduce the cost of controlling such vegetation.

Another object is the provision of methods for controlling undesired vegetation in the vicinity of a seeded crop prior to emergence of the crop without damage to the crop seeds or seedlings.

Other objects, aspects and advantages of this invention will be apparent to one skilled in the art in view of the following disclosure, the drawings and the appended claims.

SUMMARY OF THE INVENTION

Briefly, the invention provides improved (1) methods of controlling vegetation, (2) methods of selectively controlling undesired vegetation in the presence of preferred crop plants, and (3) methods of controlling undesired vegetation in the vicinity of a seeded crop prior to emergence of the crop.

In one embodiment of this invention, undesired vegetation is controlled by contacting the foliage of the vegetation with an aqueous solution containing a mixture of urea and sulfuric acid. The solution contains a herbicidally effective amount of the monourea adduct of sulfuric acid, and preferably, the molar ratio of urea to sulfuric acid is within the range of about ¼ to about 7/4 so that at least about 25 percent of the sulfuric acid is present as the monourea-sulfuric acid adduct. Within this embodiment, the foliage can be dusted or otherwise contacted with a solid mixture of urea and sulfuric acid having a urea/sulfuric acid molar ratio within the described ranges, and the solid can be contacted with sufficient water on the foliage surface to produce the desired aqueous solution in-situ. Furthermore, undesired vegetation, which is susceptible to the contact herbicidal activity of the described aqueous solutions, can be eliminated selectively from the vicinity of plants that are resistant to the herbicidal activity of those solutions, by contacting the foliage of all vegetation present with the described aqueous solutions in amounts sufficient to accomplish the desired degree of control.

In another embodiment of this invention, all vegetation in the treated area can be controlled by contacting the foliage of the vegetation with the described aqueous solutions containing urea and sulfuric acid and an amount of a surfactant which is chemically stable in the solution sufficient to increase the herbicidal activity of the composition.

The novel methods of this invention can also be used to control established vegetation in the vicinity of a seeded crop prior to emergence of the crop by contacting the foliage of the established vegetation with the described aqueous solutions. The herbicidal activity of the described herbicidal compositions rapidly dissipates upon contact with the soil so that a seeded crop, even one susceptible to the herbicial activity of the described compositions, is not damaged, provided that the herbicide is applied at least 24 hours prior to emergence.

Selective control of undesired vegetation can also be accomplished by the novel methods of this invention even in the presence of desired vegetation which itself is susceptible to the herbicidal activity of the urea-sulfuric acid compositions, by first selectively coating the foliage of the desired vegetation with a nonphytotoxic, hydrophobic oil and then contacting the foliage of all vegetation in the vicinity with the described urea-sulfuric acid compositions. The hydrophobic oil protects the desired vegetation from the herbicidal activity of the area-sulfuric acid compositions.

One surprising feature of the present invention is that, when the urea-sulfuric acid compositions herein are utilized for selectively controlling undesired vegetation, not only is such vegetation eliminated, but the urea-sulfuric acid composition subsequently becomes a rich fertilization source for desired plants. For example, it has been found in an onion field overgrown with weeds such as shepherds purse, that treatment with the urea-sulfuric acid compositions herein selectively and relatively rapidly (e.g., within 8 hours) kills the weeds. The onion plants, however, are protected by waxy vuticle coatings, and, subsequently, due to the fertilization properties of the urea-sulfuric acid composition, the onion yield is increased by as much as 30 percent or more. Similar results are obtainable with other crops, such as broccoli, which are protected by waxy cuticle coatings.

The described urea-sulfuric acid compositions containing a significant amount of the monourea-sulfuric acid adduct are surprisingly active contact herbicides, particularly toward plant foliage that is not protected by a significant coating of waxy cuticle. The presence of the surfactant in the described compositions makes them herbicidally active even toward plants that are protected by waxy cuticle. The monourea adduct-containing compositions are substantially more herbicidally active than either sulfuric acid, the diurea-sulfuric acid adduct, or combinations of the diurea adduct and free urea, when compared at equivalent sulfuric acid dosage rates.

While the described methods are more herbicidally effective than are methods employing sulfuric acid or alternative urea-sulfuric acid compositions, they are also relatively safe as compared to methods employing sulfuric acid and are much safer and have fewer ecotoxic effects than methods involving the use of other known contact herbicides. Furthermore, since the herbicidal activity of the urea-sulfuric acid compositions employed in the novel methods of this invention is not persistent, these methods can be used to control vegetation in the presence of seeded crops or food crops without damaging the desired crop or introducing potentially toxic components into the desired crop. The preferred urea-sulfuric acid compositions employed in the methods of this invention are also free of decomposition products that result from the decomposition of urea and/or sulfuric acid such as sulfamic acid and ammonium sulfamate. Thus, these methods do not introduce such decomposition products into the environment or into a crop that is established in, seeded in, or which is subsequently planted in the treated area.

BRIEF DESCRIPTION OF THE DRAWINGS

This invention will be more readily understood by reference to the drawing which is a ternary-phase diagram of the urea, sulfuric acid, and water system illustrating isotherms at several different temperatures, the existence of three prominent eutectics along those isotherms, and the boundaries for the compositions employed in the methods of this invention.

DETAILED DESCRIPTION OF THE INVENTION

Figure 1:
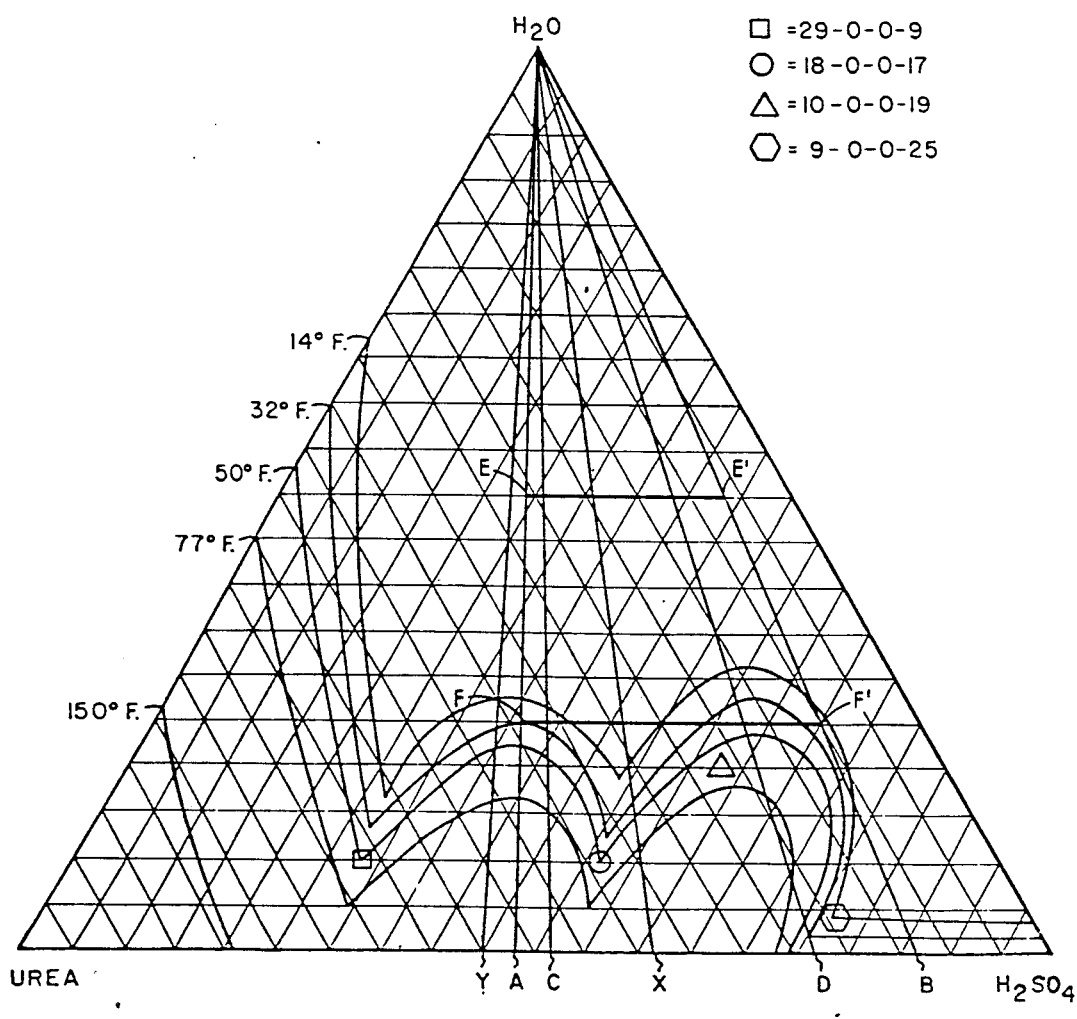

This invention provides novel methods for controlling vegetation by contacting the foliage of the vegetation with an aqueous solution containing urea and sulfuric acid. The compositions employed in the methods of this invention can be either solid or liquid, and they contain a combination of urea and sulfuric acid in which the molar ratio of urea to sulfuric is within the range of about ¼ to about 7/4 so that at least about 25 percent of the sulfuric is present as the monourea-sulfuric acid adduct. The compositions employed in the methods of this invention may optionally contain a surfactant when a broader spectrum of herbicidal activity is desired, i.e. when it is desired to control plants that might otherwise be resistant to the urea-sulfuric acid compositions. The methods of this invention that involve the use of surfactant-free compositions can be employed to selectively eliminate vegetation that is susceptible to the herbicidal activity of those compositions from the vicinity of desired vegetation that is resistant to the herbicidal activity of those compositions. The described methods can also be employed, in the presence or absence of surfactants, to control established weed populations in areas seeded with a desired crop prior to crop emergence without damage to the seeded crop. They may also be employed to eliminate undesired vegetation from the vicinity of desired plants which desired plants are also susceptible to the herbicidal activity of the urea-sulfuric acid compositions, by first treating the foliage of the desired plants with an amount of a nonphytotoxic hydrophobic oil sufficient to prevent direct contact of the urea-sulfuric acid compositions employed in the methods of this invention with the foliage of the desired vegetation.

The methods of this invention can be used to accomplish immediate pre- and post-emergent control of essentially any form of vegetation, particularly when surfactants are employed in the urea-sulfuric acid compositions used in the methods of this invention. Complete control of more resistant vegetation may require higher concentrations and/or higher dosage rates of the urea-sulfuric acid compositions. Thus, the methods of this invention can be used for either general or selective control of a wide variety of vegetation including all varieties usually found in agricultural fields such as bushes, scrubbrush, vines, weeds, and other forms of undesired plants.

Illustrative of vegetation that can be controlled by these methods, with or without the use of surfactants are: black mustard (*Brassica nigra*), curly dock (*Rumex* crispus), common groundsel (*Senecio vulgaris*), pineapple weed (*Matricaria matricarioides*), swamp smartweed (kelp) (*Polygonum coccineum*), prickly lettuce (*Lactuca scariola*), lance-leaved groundcherry (*Physalis lanceifolia*), annual sowthistle (*Sonchus oleraceus*), london rocket (*Sisymbrium irio*), common fiddleneck (*Amsinckia intermedia*), hairy nightshade (*Solanum sarrachoides*), shepherd's purse (*Capsella bursa-pastoris*), sunflower (*Helianthus annuws*), common knotweed (*Polygonum aviculare*), green amaranth (*Amaranthus hybridus*), mare's tail (*Conyza canadensis*), henbit (*Lamium amplexicaule*), cocklebur (*Xanthium strumarium*), cheeseweed (*Malva parviflora*), lambsquarters (*Chenopodium album*), puncture vine (*Tribulus terrestris*), common purslane (*Portulaca oleracea*), prostrate spurge (*Euphorbia supina*), telegraph plant (*Heterotheca grandiflora*), carpetweed (*Mollugo verticillate*), yellow starthistle (*Centaurea solstitialis*), milk thistle (*Silybum marianum*), mayweed (*Anthemis cotula*), burning nettle (*Urtica urens*), fathen (*Atriplex patula*), chickweed (*Stellaria media*), scarlet pimpernel (*Anagallis arvensis*), redroot pigweed (*Amaranthus retroflexus*), minners lettuce (*Montia perfoliata*), turkey mullein (*Eremocarpus setigerus*), nettleleaf goosefoot (*Chenopodium murale*), prostrate pigweed (*Amaranthus blitoides*), silverleaf nightshade (*Solanum elaeagnifolium*), hoary cress (*Cardaria draba*), largeseed dodder (*Cuscuta indecora*), California burclover (*Medicago polymorpha*), horse purslane (*Trianthema portulacastrum*), field bindweed (*Convolvulus arvensis*), russian knapweed (*Centaurea repens*), flax-leaved fleabane (*Conyza bonariensis*), wild radish (*Raphanus sativus*), tumble pigweed (*Amaranthus albus*), stephanomeria (*Stephanomeria exiguan*), wild turnip (*Brassica campestris*), buffalo goard (*Cucurbita foetidissima*), common mullein (*Verbascum thapsus*), dandelion (*Taraxacum officinale*), spanish thistle (*Xanthium spinosum*), chicory (*Cichorium intybus*), sweet anise (*Foeniculum vulgare*), annual yellow sweetclover (*Melilotus indical*), poison hemlock (*Conium maculatum*), broadleaf filaree (*Erodium botrys*), whitestem filaree (*Erodium moschatum*), redstem filaree (*Erodium cicutarium*), ivy-leaf morning-glory (*Ipomea hederacea*), shortpod mustard (*Brassica geniculata*), buckhorn plantain (*Plantago lacenolata*), sticky chickweed (*Cerastium viscosum*), himalaya blackberry (*Rubus procerus*), purslane speedwell (*Veronica peregrina*), mexicantea (*Chenopodium ambrosioides*), spanish clover (*Lotus purshianus*), australian brassbuttons (*Cotula australis*), goldenrod (*Solidago californica*), citron (*Citrullus lanatus*), hedge mustard (*Sisymbrium orientale*), black nightshade (*Solanum nodiflorum*), chinese thornapple (*Datura ferox*), bristly oxtongue (*Picris echioides*), bull thistle (*Cirsium vulgare*), spiny sowthistle (*Sonchus asper*), tasmanian goosefoot (*Chenopodium pumilio*), goosefoot (*Chenopodium botrys*), wright groundcherry (*Physalis acutifolia*), tomatillo groundcherry (*Physalis philadelphica*), pretty spurge (*Euphorbia peplus*), bitter apple (*Cucumis myriocarpus*), indian tobacco (*Nicotiana bigelovii*), common morning-glory (*Ipomoea purpurea*), waterplantain (*Alisma triviale*), smartweed (*Polygonum lapathifolium*), mature sowthistle (*Sonchus asper*), yellow nutsedge (*Cyperus esculentus*), purple nutsedge (*Cyperus rotundus*), lupine (*Lupinus formosus*), and grasses of the family Gramineae such as annual rye grass, blue grass, water grass, barnyard grass, bermuda grass, fescue, mat grass, Johnson grass, and the like.

The urea-sulfuric acid component of the compositions employed in the methods of this invention are reaction products of urea and sulfuric acid in which at least 25 percent of the sulfuric acid is present as the monoureasulfuric acid adduct. They may be either solids or aqueous solutions of such mixtures.

The four-digit composition designations used herein for the urea-sulfuric acid component, e.g., 18-0-0-17, are conventionally used in the agricultural industry to designate the concentration of nitrogen, phosphorus (as $P_2O_5$), potassium (as $K_2O$), and a fourth component—in this case sulfur, expressed as the element. Thus, the composition 18-0-0-17 contains 18 weight percent nitrogen derived from urea and 17 weight percent sulfur derived from sulfuric acid. Using the atomic weights for nitrogen (14.01) and sulfur (32.07) and the molecular formulas and molecular weights for urea (60.06) and sulfuric acid (98.08), it can be determined that this composition contains 38.6 weight percent urea and 52.1 weight percent sulfuric acid. By difference, the composition contains 9.3 weight percent water. The concentrations of sulfuric acid and urea in all other compositions can be determined by the same procedure.

The compositions and some crystallization temperatures of urea-sulfuric acid solutions useful in the methods of this invention are illustrated in the ternary phase diagram of the drawing. The phase diagram defines the relative proportions in weight percent for each of the three components—urea, sulfuric acid, and water—at any point within the diagram. At each apex of the triangle the system consists completely of the indicated component. Thus, the urea concentration at the urea apex is 100 percent and diminishes linearly to 0 along a straight line from the urea apex to the $H_2O-HSO_4$ boundary line, i.e., the side of the triangle opposite the urea apex. The same is true of the remaining two components: water and sulfuric acid.

The diagram also illustrates the isotherms for the system at 14° F., 32° F., 50° F., 77° F., and 150° F. The 150° F. isotherm is illustrated only partially at the lower left-hand portion of the diagram. Each isotherm defines liquid compositions which, if cooled below the temperature indicated for the respective isotherm, will precipitate components of the system. However, the solutions will super-cool dramatically, e.g., by as much as 50° F., or more, under quiescent conditions in the absence of seed crystals, impurities, etc., that promote crystallization.

As indicated by the pattern of the isotherms, systems having a fixed ratio of urea to sulfuric acid become more stable at lower temperatures as the water concentration is increased. This is true throughout most of the phase diagram with the exception of the region in the vicinity of the higher acid eutectic in the lower right-hand portion of the phase diagram.

Three prominent eutectics are apparent within the region of the illustrated isotherms. Each eutectic represents a discontinuity in the response of the system, e.g., of crystallization point, to changes in solute concentration, and indicates the points of maximum solute concentration for a given isotherm in the regions of the phase diagram associated with those eutectics.

As indicated in the legend on the drawing the left-hand eutectic on the 50° F. isotherm corresponds to the formulation 29-0-0-9. The middle eutectic on the same isotherm corresponds to the composition 18-0-0-17. The right-hand eutectic on the 14° F. isotherm corresponds to 9-0-0-25, and the formulation intermediate the 50° F. and the 77° F. isotherms between the middle and right-hand eutectics indicated by a triangular designation corresponds to 10-0-0-19.

The bold horizontal lines E—E' and F—F' within the diagram prescribe the bounaries of concentrated urea-sulfuric acid compositions that are preferable from the standpoint of manufacture and packaging prior to dilution for use. Compositions falling below line E—E' have solute, i.e., urea and sulfuric acid, concentrations of 50 weight percent or higher. Compositions falling below line F—F' located at the 25 percent water line, contain 75 weight percent of a combination of urea and sulfuric acid, or more. It can be readily seen that the four specific compositions designated in the diagram contain more than 75 weight percent solute.

Bold lines running between the urea-sulfuric acid boundary (the lower boundary of the diagram) and the water apex, generally prescribe the operable and preferred urea-sulfuric acid component compositions employed in the methods of this invention. Line Y defines compositions having a 2/1 urea/sulfuric acid molar ratio. This line intersects the urea-sulfuric acid boundary at a point corresponding to approximately 55.0 weight percent urea. Compositions falling to the left of line Y do not contain any amount of the monourea-sulfuric acid adduct; they consist of combinations of the diurea adduct and excess urea. Such compositions have little or no contact herbicidal activity in comparison to the monourea adduct. Compositions falling to the right of line Y contain at least some of the monourea adduct, and the concentration of that adduct increases as the composition approaches line X. Compositions falling on line X have urea/$H_2SO_4$ molar ratios of 1/1 and correspond to those in which both the urea and sulfuric acid are present only as the monourea-sulfuric acid adduct. Line X intersects the urea-$H_2SO_4$ boundary at a urea concentration of 38.0 weight percent.

Compositions falling between lines A and B are those in which at least 25 percent of the sulfuric acid is present as the monourea-sulfuric acid adduct. In compositions falling on line A, 25 percent of the sulfuric acid is present as the monourea adduct and 75 percent is present as the diureasulfuric acid adduct. In compositions falling along line B, 25 percent of the sulfuric acid is present in the monourea adduct and 75 percent is present as free sulfuric acid. Line A intersects the urea-sulfuric acid boundary at a point corresponding to 51.9 weight percent urea; line B intersects the same boundary at the 13.2 weight percent urea level.

In compositions falling between lines C and D, at least 50 percent of the sulfuric acid is present as the monourea adduct. Line C defines compositions in which 50 percent of the sulfuric acid is present as the monourea adduct and 50 percent is present as the diurea-sulfuric acid adduct. Compositions falling on line D correspond to those in which 50 percent of the sulfuric acid is uncomplexed, free sulfuric acid. Lines C and D intersect the urea-sulfuric acid boundary at points corresponding to 47.9 and 23.4 weight percent urea, respectively.

The 18-0-0-17 composition, and close approximations such as 17-0-0-17, are convenient formulations to manufacture for use in the methods of this invention. They have the highest solute concentrations obtainable—approximately 90 percent urea and sulfuric acid—for compositions within the desired range having reasonably low crystallization points, e.g., 50° F. Deviation from the exact 1/1 adduct, e.g., to the 17-0-0-17 formulation, is sometimes desired for manufacturing convenience as discussed hereinafter. While the 17-0-0-17 formulation has a urea-sulfuric acid molar ratio of approximately 1.05/1, that ratio is sufficiently close to the preferred ratio of 1/1 to bring the formulation within the most preferred composition range.

The minor compromise in urea-sulfuric acid ratio represented by the 18-0-0-17 and 17-0-0-17 formulations is sometimes justified by the fact that compositions having 50° F. crystallization temperatures and 1/1 urea/sulfuric acid molar ratios would contain only about 85 weight percent solute. Thus, the minor variation in molar ratio allows the production of compositions closer to the eutectic point having the same crystallization temperature and approximately 5 percent higher solute concentration.

The urea-sulfuric acid component can be produced by the reaction of urea and sulfuric acid and, optionally water, by either batch or continuous processes. The more concentrated solutions, i.e., those containing less than 25 weight percent, preferably less than 15 weight percent water, are particularly preferred for purposes of manufacture, storage and shipment. Also, the urea-sulfuric acid component is preferably substantially or completely free of decomposition products of urea and/or sulfuric acid such as sulfamic acid, ammonium sulfamate, ammonium sulfate, etc., to assure that the preferred liquid and solid herbicidal compositions employed in the methods of this invention are also free of such decomposition products. The absence of decomposition products in the urea-sulfuric acid component also assures that the sulfuric acid activity of that component has not been degraded by decomposition. Decomposition of the sulfuric acid decreases the amount of acid in the urea-sulfuric acid component available to combine with the urea to form the herbicidally active monourea-sulfuric acid adduct. Sulfuric acid decomposition also reduces the amount of acid available to perform other beneficial functions such as neutralization of soil alkalinity, improving nutrient availability to plants, etc. Urea-sulfuric acid components free of decomposition products can be produced by the reaction of solid urea and concentrated sulfuric acid by the methods described in my copending application Ser. No. 318,629 filed Nov. 5, 1981, the disclosure of which is incorporated herein by reference.

The monourea sulfuric acid adduct contained in the urea-sulfuric acid component employed in the methods of this invention is the most herbicidally active form of the urea-sulfuric acid combination. The diurea-sulfuric acid adduct exhibits much less, if any, contact herbicidal activity. Although excess sulfuric acid, i.e., free sulfuric acid, does exhibit some herbicidal activity, it is less active than an equivalent amount of sulfuric acid combined with urea to form the monourea-sulfuric acid adduct. Accordingly, the most preferred compositions are those in which essentially all of the urea and sulfuric acid are present as the monourea-sulfuric acid adduct. Such compositions have a urea/sulfuric acid molar ratio of 1/1. Compositions containing substantial amounts of either the diurea adduct or free sulfuric acid can be employed although they are not as active as the compositions having urea/sulfuric acid molar ratios of 1/1 in the methods of this invention.

As indicated above, unreacted, free sulfuric acid is undesirable in most cases since it is not as effective a contact herbicide as is the monourea adduct on an equivalent acid basis. Also, free sulfuric acid is more corrosive to equipment and human skin and thus is more difficult to handle. It has a greater tendency than does the monourea-sulfuric adduct to damage preferred crops, and thus is less desirable in the selective method embodiments of this invention. Free acid also can react chemically with other components of the compositions employed in this invention such as surfactants plant nutrients, soil adjuvants and the like. Thus, the preferred solid and aqueous compositions are those in which at least about 75, usually at least about 85, and most preferably at least about 90 percent of the sulfuric acid is present as the mono- and/or diurea-sulfuric acid adduct. Particularly preferred compositions are those that contain essentially no free sulfuric acid; thus, essentially 100 percent of the sulfuric acid would be combined with urea as the mono- and/or diurea adduct. Furthermore, since the monourea adduct is the most active combined form of urea and sulfuric acid, at least about 25, usually at least about 50, preferably at least about 70, and most preferably about 80 to about 100 percent of the sulfuric acid is present as the monourea-sulfuric acid adduct.

The monourea-sulfuric acid adduct is an active contact herbicide, even in very dilute aqueous solutions and can be used to control a variety of vegetation even in the absence of other herbicides. For instance, the 17-0-0-17 composition which contains about 85 weight percent urea and sulfuric acid on a combined weight basis, as produced, can be diluted by as much as 200 to 1 with water to produce herbicidally active solutions containing less than 0.5 weight percent solute. Even higher dilution ratios can be employed but are not preferred due to the difficulty involved in applying a sufficient amount of the active monourea adduct to crop foliage with extremely dilute solutions.

Although the monourea adduct appears to dissociate to urea and sulfuric acid in solutions containing significantly less than about 0.5 weight percent combined urea and sulfuric acid, the dissociated components recombine to form the active adduct on the foliage of treated vegetation. This is apparently due to water evaporation and consequent concentration of the urea and sulfuric acid.

Very low monourea adduct concentrations, e.g., 0.2 percent, or less, do not allow for sufficient dosage rates to provide adequate contact herbicidal activity in many instances. Thus, the applied solutions will usually contain at least about 0.5, generally at least about 1, preferably at least about 5, and most preferably at least about 10 weight percent urea and sulfuric acid based on the combined weight of those two components.

The concentrated solutions, e.g., those having urea-sulfuric acid concentrations of 85 percent or higher, are very active contact herbicides. However, they are difficult to apply evenly over the foliage due to the relatively low dosage rates required and to their relatively high viscosity.

With these factors in mind, the applied solution will usually contain about 0.5 to about 90, normally about 1 to about 90, and preferably about 5 to about 80 weight percent urea and sulfuric acid on a combined weight basis.

It is preferable to manufacture solutions containing relatively high concentrations of urea and sulfuric acid in order to avoid handling and transporting significant amounts of water. Thus, the liquid compositions, as produced, usually contain at least about 50 and preferably at least about 70 weight percent urea and sulfuric acid on a combined weight basis.

The useful and preferred concentrations of urea and sulfuric acid, and of the mono- and diurea adducts relative to each other, can also be expressed in terms of the urea/sulfuric acid molar ratio. This ratio will be the same in the solid compositions useful in this invention as it is in aqueous solutions made by dissolving those solid compositions in water, and will usually be within the range of about ¼ to about 7/4, preferably about ½ to about 3/2, and most preferably about 1/1 to about 3/2. Urea/sulfuric acid molar ratios within the range of about 1/1 to about 3/2 define compositions containing essentially no uncomplexed sulfuric acid in which at least 50 percent of the sulfuric acid is present as the monourea-sulfuric acid adduct.

A composition having a urea/sulfuric acid molar ratio of 3/2 contains 3 moles of urea for every 2 moles of sulfuric acid. Assuming complete reaction between the urea and sulfuric acid (which is essentially always the case), 50 percent of the sulfuric acid is present as the diurea-sulfuric acid adduct and 50 percent is present as the monourea adduct. Similarly, in a composition having a urea/sulfuric acid ratio of ½, 50 percent of the sulfuric acid is present as the monourea-sulfuric acid adduct and 50 percent is unreacted "free" acid.

The compositions employed in the methods of this invention may also contain one or more chemically stable surfactants. Surfactants increase the herbicidal activity of the urea-sulfuric acid component toward susceptible vegetation and broaden the spectrum of plant species that can be controlled by the methods of this invention. Surfactants increase the wetting ability of the liquid urea-sulfuric acid compositions for plant foliage, particularly for the foliage of plants that are coated with a significant amount of waxy cuticle, and facilitate the distribution of those compositions to treated foliage and to the soil by spraying or by other means.

The selected surfactant should be sufficiently chemically stable in both the solid and liquid compositions to assure that the surfactant retains its wetting ability for the period of time required to manufacture, store, transport, and apply the compositions. The stability of any surfactant can be readily determined by adding an amount of the surfactant to the urea-sulfuric acid composition in which it is to be employed, and monitoring the combination by nuclear magnetic resonance (NMR). NMR can be used to monitor the frequency and magnitude of spectral peaks characteristic of a selected nucleus, e.g., a hydrogen nucleus, in the subject molecule; i.e., in the surfactant. Persistent spectral peak magnitude and frequency over a period of 5 to 6 hours indicate stability. Diminished magnitude or a shift in peak frequency associated with the selected nucleus indicates instability, i.e., that the arrangement of functional groups in the surfactant molecule has been modified.

Illustrative of classes of stable surfactants are nonionics such as the alkylphenol polyethylene oxides, anionics such as the long chain alkyl sulfates, and cationics such as 1-hydroxyethyl-2-heptadecenyl gloxalidin. Of these, the polyethylene oxide nonionic surfactants are particularly preferred. Illustrative of preferred specific surfactants is the nonionic surfactant marketed by Thompson-Hayward, Inc., under the trademark T-MULZ 891.

The surfactant concentration should be sufficient to increase the foliage wetting ability of the aqueous solution. Increased wetting ability markedly increases both the degree and spectrum of contact herbicidal activity of the urea sulfuric acid component.

Surfactant concentration will usually be at least about 0.05, generally at least about 0.1, and preferably at least about 0.2 weight percent of the aqueous solution as applied. Surfactant concentrations of about 0.2 to about 1 weight percent are adequate in most applications. The concentration of surfactant in the solid compositions employed in one embodiment of this invention should be sufficient to produce the desired concentration in the aqueous solution that is to be produced by dissolving the solid in water. For example, a solid urea-sulfuric acid composition that is to be dissolved to produce an aqueous solution containing 5 weight percent of a combination of urea and sulfuric acid would be diluted by a factor of 19 to 1 in order to produce that solution. Thus, the solid composition should contain approximately 19 times the surfactant concentration desired in the solution on a weight percent basis. Hence, if a final solution surfactant concentration of 0.1 weight percent is desired, the solid composition should contain approximately 1.9 weight percent of that component.

The solid and liquid compositions employed in the methods of this invention can also contain any one or more of the known major and minor plant nutrients and/or soil adjuvants such as phosphorus (from phosphoric acid), magnesium, manganese, potassium, zinc, boron, etc., derived from the respective oxides, hydroxides, sulfates, nitrates, and the like. They may also contain nitrogen and/or sulfur in addition to that present in the urea and sulfuric acid. Illustrative of other forms of nitrogen and sulfur that can be used are the nitrates such as magnesium nitrate, ammonium compounds such as ammonium phosphate, sulfates such as potassium and ammonium sulfate, and the like. The concentration of these additional major and minor nutrients in the liquid and solid compositions employed in the methods of this invention should be sufficient to introduce the desired amount of the selected nutrients into the soil.

Taking all of the aforegoing factors into account, the liquid herbicidal compositions employed in the methods of this invention will comprise about 0.5 to about 90, generally about 1 to about 90, and preferably about 5 to about 80 weight percent of the combination of urea and sulfuric acid [on a dry-weight basis]; and, optionally, at least about 0.5, generally at least about 0.1, and preferably at least about 0.2 weight percent of one or more surfactants that are chemically stable in the composition. The lower concentrations of the urea-sulfuric acid component are sometimes preferred for application to vegetation and the higher concentrations are preferred for manufacture, transport and storage. Higher concentrations of the surfactant component are preferred in the concentrated solutions of the urea-sulfuric acid component to assure the presence of effective concentrations of all components if the composition is diluted with water prior to application.

The solid compositions employed in some embodiments of this invention usually contain at least about 50, and preferably at least about 80 weight percent of the urea-sulfuric acid component. The solids will usually contain at least about 20, generally at least about 50, preferably at least about 80 weight percent of the preferred monourea-sulfuric acid adduct. They also usually contain sufficient amounts of the optional surfactant component to assure the presence of an effective concentration of that component in aqueous solutions produced by dissolving the solid compositions in water prior to or during contact with the foliage of vegetation. Thus, the concentration of the surfactant component, when used in the solid compositions, will correspond to at least about 0.05, usually at least about 0.1, and preferably at least about 0.2 weight percent of the solid composition.

The solid compositions employed in the methods of this invention containing one or more surfactants (when desired), and/or additional nutrients, can be obtained by crystallizing them from their respective aqueous solutions. The surfactant and/or nutrient, when present, will either crystallize at approximately the same temperature or will be entrained with the crystallized urea-sulfuric acid component. In the alternative, the surfactant and/or nutrient, can be added to the dried or damp urea-sulfuric acid component by any suitable mixing technique after crystallization of the urea-sulfuric acid component from solution.

The 18-0-0-17 composition crystallizes at 50° F. The 10-0-0-19 composition crystallizes at about 42° F., and the 9-0-0-25 composition crystallizes at 14° F., as indicated by the crystallization curves in the drawing. Crystallization points for other compositions can be determined from the drawing, or by cooling the selected solution until crystallization occurs. The optional surfactant component usually will not significantly affect the crystallization point. The crystallized material can be separated from the supernatant aqueous phase by filtration or by decanting excess liquid, and drying.

Since lower crystallization temperatures are required to separate the desired urea-sulfuric acid component from the more dilute solutions, it is preferable to begin with more concentrated solutions having higher crystallization points such as the 18-0-0-17 composition which contains only about 10 percent water. More concentrated solutions, and those having higher crystallization temperatures such as solutions on the 77° F. crystallization curve, are even more preferred since less cooling is required to obtain a similar quantity of the urea-sulfuric acid component.

Substantially anhydrous solid compositions can be obtained by washing the dried, crystallized urea-sulfuric acid component with a strongly hydrophillic solvent such as absolute ethanol or acetone. Ten to 100 weight parts solvent per weight part solute are usually adequate for this purpose.

The monourea adduct-containing component is stable at ambient conditions and has negligible vapor pressure up to its decomposition temperatures of about 300° F. in the absence of water. Decomposition temperatures of the anhydrous solids do not change significantly with composition. These compositions decompose almost explosively at much lower temperatures, e.g., 176° F. and below, in the presence of water. The most preferred solid composition consisting of the 1/1 urea/sulfuric acid molar adduct has a melting point of about 100° F., and the melting point of the urea-sulfuric acid component increases as the urea/acid ratio deviates from 1:1 in either direction in a manner paralleling the crystallization curves in the drawing.

The liquid herbicidal compositions employed in the methods of this invention can be produced by any method capable of producing a solution of the desired composition. Thus, the surfactant and/or other components, when used, can be added to the concentrated urea-sulfuric acid solution during or immediately after its manufacture by the process described in my copending application Ser. No. 318,624, referred to above, or they can be added to the diluted urea-sulfuric acid solution prior to application of the herbicidal composition to the plants and/or soil to be treated. Alternatively, the optional components can be mixed with the amount of water required to produce a concentrated or dilute aqueous solution, as desired, before or concurrently with the solid or concentrated aqueous urea-sulfuric acid component. Of course, dissolution of the solid compositions of this invention that contain both the urea-sulfuric acid component and the desired optional components, in water, will also result in formation of the herbicidally active liquid compositions of this invention.

In the methods of this invention, the novel liquid or solid herbicidal compositions referred to above are contacted with the foliage of plants to be controlled by spraying, dusting, or otherwise distributing the liquid or solid composition onto the foliage.

When the solid compositions of this invention are applied directly to the foliage, steps should be taken to assure mixing of the solid composition with water either immediately upon or shortly after its application. This can be achieved by any one of several procedures including prewetting the foliage with water, wetting the foliage shortly after application of the solid herbicidal compositions, and the like. When the solid is applied to relatively dry foliage, it is preferably wet with sufficient water to assure formation of an aqueous solution of the urea-sulfuric acid component on the foliage within 24 hours, preferably within 10 hours, and most preferably within 1 hour following application of the solid.

In the presently preferred method, the novel liquid compositions of this invention are applied directly to the foliage rather than being formed in situ from the applied solid. When the optional components are employed, e.g., surfactants, etc. aqueous solutions of the combination of components may be performed and applied to the foilage, as such, or they can be formed in situ by sequential or simultaneous application of two or more solutions which when combined, form the desired composition. Thus, for example, a urea-sulfuric acid solution and a surfactant-containing solution can be sequentially applied to the foilage to be treated at respective dosage rates correlated to provide a combination that forms the desired solution in situ. It is essential only that the vegetation to be treated be contacted with the described compositions at effective dosage rates. Nevertheless, for convenience and ease of application and control, the use of preformed solutions containing all of the desired components is presently preferred.

The methods of this invention can also be employed to eliminate undesired vegetation from fields seeded with desired crop plants prior to crop emergence. The contact herbicidal activity of urea-sulfuric acid component dissipates rapidly upon exposure to the soil environment, i.e., within about 24 hours or less. Thus, crop seeds and unemerged seedlings are not damaged when the urea-sulfuric acid component is applied, even after germination, particularly when the herbicidal composition is applied at least 24 hours prior to emergence.

The compositions of this invention containing one or more surfactants and the urea-sulfuric acid component can be used to eliminate essentially all vegetation from the treated area. Even minor amounts of surfactant dramatically increase the contact herbicidal activity of the urea-sulfuric acid component and the spectrum of plant varieties it controls. The activity of the urea-sulfuric acid component increases as surfactant concentration is increased within the ranges discussed above to the point that the compositions of this invention that contain a significant amount of surfactant, e.g., 0.1 weight percent surfactant as applied, are essentially nonselective. Thus, the methods employing surfactant-containing compositions can be used to control the more resistant plant varieties, such as volunteer wheat and Russian thistle.

The methods of this invention that do not involve the use of a significant amount of surfactant, e.g., less than 0.05 weight percent surfactant as applied, can be used to selectively control susceptible plants in the presence of more resistant desirable plants, such as crop plants. The tolerance of vegetation to the surfactant-free compositions varies significantly between species. Thus, for example, relatively low dosage rates are required to eliminate morning glory while higher dosage rates and surfactants are required to kill more xerophytic plants such as onions and garlic, the foliage of which is protected by a significant amount of waxy coating or cuticle.

The foliage and stems of essentially all plants are protected, to some extent, by a waxy cuticle coating, and the degree of such protection can vary significantly from one species to the next. The contact activity of the urea-sulfuric acid component toward different plant species appears to correlate with the degree of protection afforded by the waxy cuticle on a given plant species. Thus, the effect of surfactant on contact activity may be associated with the surfactant's ability to transport the urea-sulfuric acid component through the protective coating to the plant cell tissue.

Illustrative of crops that are sufficiently tolerant to the surfactant-free compositions to allow for the use of such less resistant, undesired vegetation in the vicinity of the crop, are onions (green and dry bulb), leeks, shallots, spring onions, garlic, chives, cotton, broccoli, cauliflower, cabbage (red and green), Brussel sprouts, Chinese cabbage, bok choy, turf, and some cereal crops such as wheat and barley. Thus, weeds that are not resistant to the herbicidal activity of the urea-sulfuric acid component can be controlled in the presence of these and other tolerant crops and plants with the methods of this invention. Alternatively, the urea-surfactant acid component, with or without surfactants, can be selectively contacted with the foliage of undesired vegetation in the presence of desired crops. However, this alternative is less preferred since it presents a greater risk of damage to the desired crop.

Undesired vegetation also can be eliminated selectively from the presence of desired crop plants by selectively applying to the crop plants an amount of a non-phytotoxic, hydrophobic oil sufficient to decrease the wetability of the crop foliage by the aqueous urea-sulfuric acid solution applied, followed by applying to the foliage of both the undesired vegetation and the oil-treated crop plants an amount of the urea-sulfuric acid solution that is herbicidally effective toward the undesired vegetation and sufficient to retard the growth of such vegetation. It is necessary only to contact the foliage of the plants to be controlled with the described urea-sulfuric acid solutions. A unique advantage of this embodiment employing a protective oil coating on the preferred plants is that it guards against damage that might otherwise occur to the crop and even enables the elimination of more resistant weeds from crop plants that are less resistant than the weeds to the applied solution.

Surfactants reduce the degree of selectivity obtainable by the methods of this embodiment since they promote penetration of the protective hydrophobic oil coating on the crop foliage. Accordingly, the compositions employed in this embodiment preferably contain little or no surfactant. Thus, surfactant levels in these compositions are preferably below 0.05 weight percent applied.

Although significant amounts of free sulfuric acid are unpreferred, the compositions employed in this embodiment can contain limited amounts of free sulfuric acid if desired for some other purpose. Limited amounts of free sulfuric acid have little detrimental effect on crop plants protected by hydrophobic oil coatings.

A variety of nonphytotoxic hydrophobic oils are suitable for use within this embodiment. It is essential only that they be relatively water-insoluble and nontoxic to plants. Exemplary are vegetable oils and nonaromatic mineral oils. Illustrative of suitable oils within these generic classifications are cotton seed oil, corn oil, 90-neutral oil, dormant spray oil, and the like.

The hydrophobic oil should be selectively applied to the foliage of the crop plants at a rate sufficient to substantially cover the exposed foliage and protect it from the herbicidal activity of the urea-sulfuric acid solutions. Oil dosage rates suitable for this purpose depend upon the amount of exposed foliage surface of the crop plants and are usually at least about 2, and normally about 10 to about 20 gallons per acre for usual field or vine crops.

The dosage rates of the urea-sulfuric acid component employed in each embodiment of this invention should be sufficient to accomplish the desired degree of control of undesired vegetation, and, in the embodiments designed for selective control of undesired vegetation in the presence of desired plants, should be insufficient to significantly damage or retard the growth or deminish the quality of the desired plants. The herbicidal compositions are usually applied at dosage rates corresponding to at least about 50, generally about 50 to about 1000, and preferably about 100 to about 500 pounds per acre of the monourea-sulfuric acid adduct. These dosage rates correspond to at least about 50, generally about 50 to about 4,000, and preferably about 100 to about 2,000 pounds per acre of the combination of urea and sulfuric acid when using the compositions in which at least about 25 percent of the sulfuric acid is present as the monourea-sulfuric acid adduct.

Relatively higher dosage rates of compositions deviating significantly from the 1/1 urea/sulfuric acid molar ratio composition are required to obtain the same degree of contact herbicidal effectiveness under otherwise identical conditions, i.e., with similar plant types. The most significant consideration in this respect is the amount of monourea-sulfuric acid adduct applied and retained on the plant foliage. Thus, higher dosage rates should be used when applying compositions in which only a portion of the sulfuric acid is present as the monourea adduct, i.e., when a significant amount of the acid is present either as the diurea-sulfuric acid adduct or as free sulfuric acid. Although free sulfuric acid has some herbicidal activity, it is much less active than the monourea-urea sulfuric acid adduct on an equivalent sulfuric acid basis.

Although the dosage rate of the urea-sulfuric acid component required to accomplish the desired control will generally be within the ranges discussed above, the dosage rate best suited to accomplish the desired degree of control, and the desired degree of selectivity (when selectivity is required) in any given case, also can be determined by actual greenhouse or field testing. Such tests may involve the application of a series of compositions having different concentrations of the urea-component and/or a series of tests in which the same composition is applied to different plots of the same plant population in a series of different dosage rates. The dosage rate required to eliminate the undesired vegetations can be readily determined by applying a series of different compositions to separate, small areas of the vegetation to be treated within the selected field, at a series of different dosage rates, and observing the extent of plant kill. When effective concentrations and dosage rates are employed, significant necrosis and plant wilting are evident within 10 minutes and will provide an adequate indication of effectiveness. The full extent of plant kill will usually be apparent within approximately 2 to 24 hours. In most situations, prescreening tests of that duration are not inordinant. Plant necrosis is clearly indicated within 24 hours by the disappearance, darkening and/or desiccation of plant tissue. The speed and degree of vegetation control increases as dosage rate is increased. Dosage rate is the primary variable so long as the applied volume is not so high that significant runoff occurs from plant foliage The methods of this invention have numerous advantages over methods of vegetation control otherwise available to the art. They effectively control a variety of vegetation by the use of compositions that do not introduce toxic materials into the environment. On the contrary, these methods result only in the addition of nutrient nitrogen and sulfur to the soil and have the additional benefit of introducing significant amounts of active sulfuric acid which effectively counteracts alkalinity that is a prevailing problem in many soils in the western United States. The urea-sulfuric acid compositions of this invention are relatively noncorrosive, both to materials and animal tissue, and thus are easier to handle than is sulfuric acid and many other contact and systemic herbicides.

Since the urea-sulfuric acid component of the compositions employed in the methods of this invention are free of the decomposition products of urea and/or sulfuric acid, including decomposition products of the urea-sulfuric acid adducts, the sulfuric acid value of the compositions employed in these methods is not depleted. Thus, these methods result in the addition of the maximum amount of sulfuric acid to the plants and to the soil for any given dosage rate of the specific composition. Furthermore, the absence of decomposition products in the compositions employed in the methods of this invention assures that these methods will not result in the addition of toxic materials such as sulfamic acid, ammonium sulfamate and other potentially toxic decomposition products of urea and sulfuric acid.

The methods of this invention afford the applicator and grower with a greater degree of flexibility than is available with other methods of vegetation control, since they can be employed either to selectively eliminate undesired vegetation from the presence of desired vegetation such as crops, etc., or, in the alternative, can be employed to eliminate essentially all of the vegetation in the treated area. The methods of this invention involving the use of surfactants result in broad spectrum control of all the vegetation to which the described urea-sulfuric acid compositions are foliarly applied. Surfactants dramatically increase the herbicidal activity of the urea-sulfuric acid component employed in the methods of this invention and increase the variety of plants that can be controlled by these methods to encompass all plant species.

The methods of this invention have the further advantage of employing either solids or liquids, each one of which can be employed in either concentrated or dilute form. This flexibility allows the applicator an even broader variety of choice in his selection of convenient, effective methods of application and treatment.

The invention is further described by the following examples which are illustrative of specific modes of practicing the invention and are not intended as limiting the scope of the invention as defined by the appended claims.

EXAMPLE 1

Four separate twenty-acre test plots in the vicinity of Havre, Mont. containing young wheat 8 to 10 inches in height and heavy infestations of morning glory, thistle and barnyard grass were treated by foliar application of 20 gallons per acre of 17-0-0-17 diluted with water to produce a spray volume of 50 gallons per acre. This treatment resulted in more than 99 percent kill of all weeds within 24 hours of application. There was no significant damage to the young wheat crop as evidenced by the absence of foliage loss, spotting or browning.

EXAMPLE 2

Twelve replicated test plots of commercial turf of 5 milliacres each infested with spurge and oxalis, were each treated with 17-0-0-17 at a dosage rate of 15 gallons per acre diluted with water to produce a spray volume of 50 gallons per acre. The commercial turf comprised a mixture of rye, bermuda and fescue grasses. All weeds were completely destroyed within 24 hours of application. There was no significant damage to the commercial turf crop as evidenced by the lack of foliage loss, browning or spotting.

EXAMPLE 3

Two replicated test plots of established broccoli of 5 acres each infested with maily, malva, nettle, shepherds purse and groundsel were treated by foliar application of 17-0-0-17 at a dosage rate of 10 gallons per acre diluted with water to produce a spray volume of 100 gallons per acre. Foliar application was effected by injecting the spray through the existing "drop-nozzle" irrigation system. The broccoli crop was at the 3 to 4 true leaf stage and was approximately 4 inches high. This treatment resulted in 100 percent kill of all weed species and 10 percent to 20 percent damaged area on the foliage of the broccoli crop as evidenced by foliage discoloration, e.g., browning. The broccoli crop recovered completely.

EXAMPLE 4

Two replicated test plots of 5 acres each of the broccoli crop described in Example 3 were treated by foliar application of sulfuric acid at a dosage rate equivalent to the sulfuric acid dosage rate employed in Example 3. In other words, the amount of sulfuric acid applied per acre was equal to the amount of sulfuric acid contained in the amount of 17-0-0-17 applied per acre in Example 3, i.e., 67.7 pounds of sulfuric acid per acre. This amount of sulfuric acid was diluted with water to produce a total spray volume of 100 gallons per acre prior to application as described in Example 3. This treatment resulted in 75 to 85 percent kill of all weed species, and 90 to 95 percent damage to the foliage of the broccoli crop as evidenced by foliage discoloration, loss and browning.

EXAMPLE 5

Four replicated test plots of 5 acres each comprising onions at the first true leaf stage (approximately 1 inch high) in height) infested with malva, cheeseweed, nightshade, shepherds purse, peneapple weed, and purslane were treated by foliar application of 17-0-0-17 at a dosage rate of 20 gallons per acre diluted with water to produce a total spray volume of 50 gallons per acre. This treatment resulted in 95 to 100 percent kill of all weed species within 48 hours after application. There was no damage to the onion crop as evidenced by the lack of foliage browning, spotting, etc.

EXAMPLE 6

The operation of Example 5 was repeated by application of 10-0-0-19 to 4 replicated test plots of 5 acres each of the onion crop described in Example 5. The 10-0-0-19 was applied at a dosage rate of 18.1 gallons per acre which was sufficient to produce a sulfuric acid dosage rate equivalent to the amount of sulfuric acid applied in the 17-0-0-17 employed in Example 5, i.e., 151.3 pounds of sulfuric acid per acre. This treatment resulted in 95 to 100 percent kill of all weed species and substantial damage to the onion crop as evidenced by 30 to 40 percent loss of stand, i.e., 30 to 40 percent of the onion plants were killed.

EXAMPLE 7

The operation described in Example 5 was repeated by the foliar application of 28-0-0-9 to 4 replicated test plots of 5 acres each of the onion crop described in Example 5. The 28-0-0-9 was applied at a rate of 41.3 gallons (491.9 pounds) per acre corresponding to a sulfuric acid dosage rate equivalent to that employed in Example 5, i.e., 151.3 pounds of sulfuric acid per acre. This treatment resulted in 10 to 20 percent damage to the weed foliage as indicated by spotting and browning, but only negligible, if any, weed kill, i.e., less than 10 percent kill of the established weeds. Foliage spotting and browning was probably due to the salt effect that would be expected by the application of significant amounts of any solute to the foliage of sensitive vegetation. There was no damage to the onion crop as evidenced by the absence of foliage spotting or browning.

EXAMPLE 8

The operation described in Example 5 was repeated by the foliar application of sulfuric acid to 4 replicated test plots of 5 acres each of the onion crop described in Example 5. The sulfuric acid was applied at a dosage rate of 151.3 pounds per acre which was equivalent to the amount of sulfuric acid contained in the 17-0-0-17 employed in Example 5 on a per acre basis. Prior to broadcast application the sulfuric acid was diluted with water to provide a total spray volume of 50 gallons per acre. This treatment resulted in 75 to 80 percent kill of all weed species and 50 to 60 percent loss of the onion crop.

The conditions employed and the results obtained in Examples 5 through 8 are summarized in Table 1.

TABLE 1

| Example Number | Composition | Dosage[1] gal./@ | Spray Volume. gal/@ | Percent Kill Weeds | Percent Kill Onions |
|---|---|---|---|---|---|
| 5 | 17-0-0-17 | 20 | 50 | 95–100 | None |
| 6 | 10-0-0-19 | equivalent | 50 | 95–100 | 30–40 |
| 7 | 28-0-0-9 | equivalent | 50 | negligible 10% | None |
| 8 | $H_2SO_4$ | equivalent | 50 | 75–80 | 50–60 |

[1] are treatments employed equivalent amounts of sulfuric acid per acre.

The results of Examples 5 through 8 illustrate that vegetation control methods employing urea-sulfuric acid compositions containing a significant proportion of the monourea-sulfuric acid adduct, i.e., 17-0-0-17 and 10-0-0-19, are much more effective than is sulfuric acid for the control of weeds, and that such compositions are also more selective as evidenced by the significantly lower damage to the onion crop that resulted from their use. Those results also indicate that urea-sulfuric acid compositions that have low $H_2SO_4$/urea molar ratios and thus do not contain any significant amount of the monourea-sulfuric acid adduct, i.e., Example 7—28-0-0-9, do not have any significant herbicidal effect on either the weeds or crop under comparable conditions. The results of Example 6 illustrate that urea-sulfuric acid compositions containing free sulfuric acid in excess of that complexed with the urea e.g., 10-0-0-19, are less preferred when selectivity is desired. Compositions such as 10-0-0-19 that contain significant amounts of the monourea-sulfuric acid adduct in combination with free sulfuric acid are very effective for the control of vegetation as evidenced by the fact that the percentage weed kill obtained with 10-0-0-19 was comparable with that obtained with 17-0-0-17. However, they are less selective as indicated by the extent of damage to the young onion crop. The 17-0-0-17 employed in Example 5 has a urea-sulfuric acid molar ratio very close to 1. Thus, essentially all of the urea and sulfuric acid in that composition are present as the monourea-sulfuric acid adduct. The composition is essentially free of uncomplexed sulfuric acid. The use of the 17-0-0-17 composition in the methods of this invention (Example 5) resulted in essentially complete weed control and no observable damage to the onion crop.

EXAMPLE 9

A weed infested test plot in a field planted with field corn was treated by foliar application of 17-0-0-17 at a dosage rate of 20 gallons per acre, diluted with water to provide a spray volume of 50 gallons per acre. The application was made one week prior to emergence of the field corn crop. Prior to treatment, the field was heavily infested with a variety of weeds including grundsel, melva, nightshade and wild musturd. The described treatment resulted in 100 percent kill of all weed species within 24 hours hrs. and 12 percent yield increase in corn harvested from the treated test plot in comparison to adjacent, untreated control areas in the same field.

EXAMPLE 10

An established weed population comprising grundsel, chickweed, sow thistle, foxtail, melva, nightshade and fiddleneck can be completely controlled by foliar application of 15 gallons per acre of 17-0-0-17 diluted with water to provide a spray volume of 50 gallons per acre containing 0.2 weight percent, based on the weight of the total spray, of the non-ionic surfactant marketed by Thompson-Hayward, Inc. under the trademark T-MULZ 891.

EXAMPLE 11

A solid herbicidal composition containing a surfactant and systemic herbicide can be prepared from an 18-0-0-17 solution having a crystallization temperature of 50° F. and containing 38.6 weight percent urea, 52.1 weight percent sulfuric acid, and 9.3 weight percent water. The 18-0-0-17 solution is cooled to a temperature of 34° F. to crystallize the solute which is then separated from the bulk of the water phase in a conventional filter press operated at 34° F. The damp solid is sequentially washed five times in five equal volumes of acetone; 2 weight-parts of acetone per weight part of the urea-sulfuric acid component are employed in each washing step. The resulting, substantially anhydrous, urea-sulfuric acid component having a composition corresponding to 19.8-0-0-18.7 is blended with Thompson-Hayward's T-MULZ 891-brand surfactant to produce a final composition containing 0.6 weight percent T-MULZ 891.

EXAMPLE 12

The surfactant-containing solid composition produced as described in Example 11 can be employed to control an established weed population of nightshade, fiddleneck, foxtail, chickweed, burrclover and sowthistle. Equal weight parts of the described solid composition and water are mixed together to produce an aqueous solution having the composition 9.9-0-0-9.35 containing 0.3 weight percent TMULZ 891-brand surfactant (0.04 pounds per gallon). The solid readily dissolves in water. The resulting solution can be foliarly applied to the established weed population at a dosage rate of 40 gallons per acre to control all weed species.

While particular embodiments of the invention have been described, it will be understood, of course, that the invention is not limited thereto since many obvious modifications can be made and it is intended to include within this invention any such modifications as will fall within the scope of the appended claims.

Having described my invention, I claim:

1. A method for controlling the growth of vegetation which comprises contacting the foliage of said vegetation with a herbicidally effective amount of a composition comprising the monourea adduct of sulfuric acid.

2. The method defined in claim 1 wherein said composition comprises phosphoric acid.

3. The method defined in claim 1 wherein said composition further comprises a surfactant.

4. The method defined in claim 1 which comprises contacting the foliage of said vegetation with (a) a composition comprising the monourea adduct of sulfuric acid and (b) a composition comprising a surfactant.

5. The method defined in claim 1 wherein said composition comprises an aqueous solution comprising said monourea adduct of sulfuric acid, and said monourea adduct of sulfuric acid is present in an amount corresponding to at least about 1 weight percent based on the combined, equivalent weights of urea and sulfuric acid.

6. The method defined in claim 1 wherein said composition comprises an aqueous solution of said monourea adduct of sulfuric acid and a surfactant containing an amount of said monourea adduct corresponding to at least about 1 weight percent equivalent combined urea and sulfuric acid.

7. The method defined in claim 1 wherein said composition is free of decomposition products of urea and sulfuric acid.

8. The method defined in claim 1 wherein said composition is free of sulfamic acid and ammonium sulfamate.

9. The method defined in claim 1 wherein said composition comprises an aqueous solution containing a surfactant and an amount of said monourea adduct of sulfuric acid corresponding to at least about 1 weight percent equivalent urea plus sulfuric acid and is free of sulfamic acid and ammonium sulfamate.

10. The method defined in claim 9 wherein said composition further comprises phosphoric acid.

11. The method defined in claim 1 wherein said vegetation comprises plants susceptible to the herbicidal activity of said composition and plants resistant to the herbicidal activity of said composition, and said composition is essentially free of surfactant and is applied to said plants at a dosage rate sufficient to control said susceptible plants and insufficient to significantly damage said resistant plants.

12. The method defined in claim 1 wherein said composition is applied to said plants as a solid composition comprising said monourea adduct of sulfuric acid, and said composition is contacted with water while in contact with said foliage.

13. The method defined in claim 1 wherein said vegetation is growing in an area seeded with a preferred crop, and said vegetation is contacted with said composition prior to the emergence of said preferred crop.

14. The method defined in claim 1 wherein said vegetation comprises desired crop plants and undesired vegetation growing in the vicinity of said crop plants, and said method comprises the steps of (1) selectively applying to the foliage of said crop plants an amount of a non-phytotoxic, hydrophobic oil sufficient to decrease the wettability of the foliage of said crop plants by said composition, and (2) contacting the foliage of at least said undesired vegetation with said composition.

15. A method for selectively controlling undesired vegetation susceptible to the herbicidal activity of the composition hereinafter defined in the presence of desired crop plants resistant to the herbicidal activity of said composition, which method comprises applying at least to the foliage of said undesired vegetation a herbicidally effective amount of a composition comprising the monourea adduct of sulfuric acid.

16. The method defined in claim 15 wherein said composition is essentially free of surfactant.

17. The method defined in claim 15 wherein said composition is free of surfactant and is applied to the foliage of said undesired vegetation and said desired crop plants at a dosage rate sufficient to significantly retard the growth of said undesired vegetation and insufficient to significantly retard the growth of said desired crop plants.

18. The method defined in claim 17 wherein said composition is free of decomposition products of urea and sulfuric acid.

19. The method defined in claim 15 wherein said desired crop plants are selected from the group consisting of onions, leeks, garlic, broccoli, brussel sprouts, cabbage, cauliflower, celery, cotton, carrots, asparagus, dormant alfalfa, dormant parsley, barley, wheat, rye, spreengle, watergrass, annual bluegrass, and combinations thereof.

20. The method defined in claim 17 wherein said desired crop plants are selected from the group consisting of onions, leeks, garlic, broccoli, cabbage and combinations thereof.

21. A method for controlling vegetation which comprises applying to the foliage of said vegetation a herbicidally effective amount of an aqueous solution comprising the monourea adduct of sulfuric acid and a surfactant.

22. A method for controlling vegetation which comprises applying to the foliage thereof a herbicidally effective amount of an aqueous solution comprising the monourea adduct of sulfuric acid and phosphoric acid.

23. The method defined in claim 22 wherein said solution further comprises a surfactant.

24. A method for controlling vegetation which comprises applying to the foliage of said vegetation a herbicidally effective amount of an aqueous solution comprising the monourea adduct of sulfuric acid and a surfactant, which solution is free of sulfamic acid and ammonium sulfamate.

25. A method for controlling vegetation which comprises applying to the foliage of said vegetation a herbicidally effective amount of an aqueous solution comprising the monourea adduct of sulfuric acid free of sulfamic acid and ammonium sulfamate.

26. The method defined in claim 25 wherein said composition further comprises phosphoric acid.

27. A method for selectively controlling undesired plants susceptible to the herbicidal activity of the composition hereinafter defined in the presence of desired crop plants resistant to the herbicidal activity of the composition hereinafter defined, which comprises applying to the foliage of said plants a composition comprising an amount of the monourea adduct of sulfuric acid sufficient to retard the growth of said undesired plants and insufficient to significantly retard the growth of said desired crop plants, said composition being essentially free of surfactant, sulfamic acid, and ammonium sulfamate.

28. The method defined in claim 1 wherein said composition is free of unadducted sulfuric acid.

29. The method defined in claim 1 wherein the equivalent urea/$H_2SO_4$ molar ratio in said composition is at least 1.

30. The method defined in claim 25 wherein said composition is free of unadducted sulfuric acid.

31. The method defined in claim 25 wherein the equivalent urea/$H_2SO_4$ molar ratio in said composition is at least 1.

32. The method defined in claim 21 wherein said composition is free of unadducted sulfuric acid.

33. The method defined in claim 21 wherein the equivalent urea/$H_2SO_4$ molar ratio in said composition is at least 1.

34. The method defined in claim 22 wherein said composition is free of unadducted sulfuric acid.

35. The method defined in claim 22 wherein the equivalent urea/$H_2SO_4$ molar ratio in said composition is at least 1.

* * * * *

UNITED STATES PATENT AND TRADEMARK OFFICE
CERTIFICATE OF CORRECTION

PATENT NO. : 5,055,127

DATED : October 8, 1991

INVENTOR(S) : Donald C. Young

It is certified that error appears in the above-identified patent and that said Letters Patent is hereby corrected as shown below:

Column 22, line 49, "25" should be -- 15 --.

Column 22, line 51, "25" should be -- 15 --.

Signed and Sealed this

Twenty-sixth Day of January, 1993

Attest:

STEPHEN G. KUNIN

*Attesting Officer*   *Acting Commissioner of Patents and Trademarks*